United States Patent [19]

Jenck

[11] Patent Number: 4,485,255

[45] Date of Patent: Nov. 27, 1984

[54] CARBONYLATION OF α,β-UNSATURATED ESTERS TO LINEAR SATURATED DIESTERS

[75] Inventor: Jean Jenck, Villeurbanne, France

[73] Assignee: Rhone-Poulenc Chimie de Base, Curbevoie, France

[21] Appl. No.: 444,886

[22] Filed: Nov. 29, 1982

[30] Foreign Application Priority Data

Dec. 1, 1981 [FR] France .................. 81 22613

[51] Int. Cl.$^3$ ............................................. C07C 67/38
[52] U.S. Cl. .................................... 560/193; 502/152; 502/167; 502/326; 560/204
[58] Field of Search .............................. 560/204, 193; 252/431 C, 431 R, 472, 441; 502/152, 167, 326

[56] References Cited

U.S. PATENT DOCUMENTS

| 4,069,388 | 1/1978 | Zehner ................................. 560/204 |
| 4,169,956 | 10/1979 | Kummer et al. ..................... 560/204 |
| 4,189,599 | 2/1980 | Kesling et al. ...................... 560/204 |
| 4,235,744 | 11/1980 | Pesa et al. ........................... 560/204 |

Primary Examiner—Natalie Trousof
Assistant Examiner—Vera C. Clarke
Attorney, Agent, or Firm—Burns, Doane, Swecker & Mathis

[57] ABSTRACT

Linear saturated diesters, e.g., dialkyl adipates, are prepared by carbonylating an α,β-unsaturated ester, e.g., an alkyl pent-2-enoate, with carbon monoxide and an alcohol, in the presence of a cobalt catalyst and a tertiary nitrogen-containing base.

20 Claims, No Drawings

CARBONYLATION OF α,β-UNSATURATED ESTERS TO LINEAR SATURATED DIESTERS

BACKGROUND OF THE INVENTION

1. Field of the Invention

The present invention relates to the preparation of linear saturated diesters by the carbonylation of α,β-unsaturated ester(s), i.e., by the reaction of carbon monoxide and an alcohol with said unsaturated ester(s).

The process according to the present invention is especially adapted for the preparation of alkyl adipates by the carbonylation of alkyl pent-2-enoates.

2. Description of the Prior Art

It is well known to this art, from *Bulletin of the Chemical Society of Japan,* Volume 46, pages 526 and 527 (1973), that a mixture containing dialkyl esters and, in particular, an alkyl adipate, is obtained by reacting carbon monoxide and an alcohol with an alkyl pent-3-enoate under high pressure and at elevated temperature, in the presence of cobalt carbonyl and an aromatic heterocyclic nitrogen-containing base. However, the industrial-scale application or development of a technique of this type, the value of which is not contested in principle, is seriously limited because of the lack of efficiency thereof.

SUMMARY OF THE INVENTION

Accordingly, a major object of the present invention is the provision of an improved, much more highly efficient process for the preparation of linear diesters having the structural formula:

$$R_3COO-CH_2-R_1)_p(CH_2)_2COOR_2 \quad (I)$$

which process featuring reacting, in liquid phase, carbon monoxide and an alcohol ($R_3OH$) with an α,β-unsaturated ester having the structural formula:

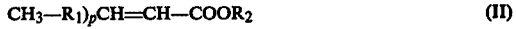

$$CH_3-R_1)_pCH=CH-COOR_2 \quad (II)$$

in which the formula $R_1$ is an alkylene radical having up to 20 carbon atoms, optionally substituted by one or two chlorine atoms or alkoxy substituents containing up to 4 carbon atoms; $R_2$ is an alkyl radical containing up to 12 carbon atoms, optionally substituted by one or two hydroxy substituents, an aralkyl substituent having from 7 to 12 carbon atoms, or a phenyl substituent; p is equal to zero or one; and $R_3$ is defined as was $R_2$ above, with $R_3$ and $R_2$ either being identical or different; in the presence of a catalytically effective amount of a metallic cobalt or cobalt compound catalyst, and in the further presence of a tertiary nitrogen-containing base.

DETAILED DESCRIPTION OF THE INVENTION

More particularly according to this invention, carbon monoxide and an alcohol are therefore reacted with an α,β-unsaturated ester having the structural formula:

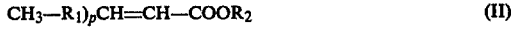

$$CH_3-R_1)_pCH=CH-COOR_2 \quad (II)$$

in which $R_1$ is an alkylene radical having up to 20 carbon atoms, optionally substituted by one or two chlorine atoms or alkoxy substituents containing up to 4 carbon atoms; $R_2$ is an alkyl radical containing up to 12 carbon atoms, optionally substituted by one or two hydroxyl substituents, an aralkyl substituent having from 7 to 12 carbon atoms, or a phenyl substituent; and p is equal to zero or one.

Preferably, p is equal to 1; $R_1$ is advantageously a radical $-CH_2)_n$, with n being an integer which is greater than or equal to 1 and less than or equal to 6, and which can contain one or two methyl substituents; and $R_2$ is more particularly an alkyl radical having up to 4 carbon atoms.

Among the α,β-unsaturated esters which are suitable starting materials for the present process, alkyl pent-2-enoates are very particularly valuable because same enable efficient obtainment of the alkyl adipates, which are intermediates in the preparation of adipic acid. Thus, it has now surprisingly and unexpectedly been found that the α,β-unsaturated esters are especially reactive in the process according to this invention, while at the same time giving rise to the preparation of the corresponding linear saturated diester in high selectivity.

The present process requires the use of an alcohol having the formula $R_3OH$, with $R_3$ being as above-defined.

Exemplary of the alcohols which are useful within the scope of the present process, representative are methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol and phenol.

It is preferred to use an alkanol having up to 4 carbon atoms; methanol and ethanol are especially suitable for carrying out the subject process.

The alcohol and the α,β-unsaturated ester can be used in stoichiometric amounts. However, it is preferred to use an excess of alcohol in the proportion of 1 to 10, or even more preferred to use from 2 to 5 mols of alcohol per mol of α,β-unsaturated ester.

The reaction is carried out in the presence of a metal catalyst selected from among cobalt and cobalt compounds. Any source of cobalt which is capable of reacting with carbon monoxide, in the reaction medium, to provide cobalt carbonyl complexes, in situ, is useful within the scope of the present invention.

Examples of typical such sources of cobalt are finely divided cobalt metal, inorganic salts of cobalt, such as cobalt nitrate or carbonate, and the organic salts thereof, in particular the carboxylates. Cobalt carbonyls or hydrocarbonyls are also representative; dicobalt octacarbonyl, for example, is eminently suitable for carrying out the process of the invention.

The molar ratio of the α,β-unsaturated ester to the cobalt advantageously ranges from 10 to 1,000. This ratio preferably ranges from 20 to 300.

The process according to the present invention also requires the presence of a tertiary nitrogen-containing base having a $pK_a$ ranging from 3 to 10.

Preferred are 5-membered or 6-membered nitrogen-containing heterocyclic compounds which can contain one or two substituents selected from among alkyl or alkoxy substituents having up to 4 carbon atoms, a hydroxyl substituent and halogen atom substituents, which optionally contain two or three double bonds, and which, if appropriate, can furthermore be fused to a benzene nucleus, with the proviso that the atoms bonded to the nitrogen hetero-atom are neither substituted nor common to two rings.

6-Membered nitrogen-containing heterocyclic compounds having a $pK_a$ ranging from 4 to 7, in particular pyridine, 4-picoline, isoquinoline, 5-lutidine and 3,4-lutidine, are more particularly suitable for carrying out the subject process.

The amount of tertiary nitrogen-containing base employed is typically such that the molar ratio N/Co ranges from 0.5 to 50. To carry out the process of the invention most satisfactorily, this ratio preferably ranges from 2 to 25.

Thus, according to the present invention, carbon monoxide and an alcohol ($R_3OH$) are reacted with an $\alpha,\beta$-unsaturated ester, in the presence of the catalyst system defined above. The reaction is carried out in the liquid phase, at a temperature which is generally above 100° C., although there is no advantage in exceeding 200° C., under a carbon monoxide pressure which is at least 50 bars and which can be as much as 1,000 bars. The reaction is preferably carried out at a temperature on the order of 130° to 180° C. and under a carbon monoxide pressure on the order of 100 to 300 bars.

Of course, the optimum conditions of pressure and temperature will be the more severe, the less reactive the starting material, and this occurs, in particular, if the degree of steric protection of the double bond increases.

Carbon monoxide is used in the substantially pure form, such as is available commercially. However, the presence of impurities, such as carbon dioxide, methane or nitrogen, is not harmful; the presence of trace amounts of hydrogen (less than 1.5% by volume) tends to stabilize the catalyst system.

As above-outlined, the process according to the present invention is well adapted for the synthesis of alkyl adipates from alkyl pent-2-enoates. Within the scope of this particular synthesis, it is advantageous to select the alcohol (co-reactant) which corresponds to the alkyl radical of the starting material ester, such alkyl radical preferably having up to 4 carbon atoms.

Good results are obtained starting from the following pairs of reactants: methyl pent-2-enoate and methanol, and ethyl pene-2-enoate and ethanol.

Although the saturated linear diester is obtained in a high selectivity, the formation of small proportions of branched saturated diesters, and of the saturated ester which is the hydrogenation product of the starting material, nevertheless also results.

In order to further illustrate the present invention and the advantages thereof, the following specific examples are given, it being understood that same are intended only as illustrative and in nowise limitative.

In said examples to follow, the following designations are used:

=/Co denotes the molar ratio of the $\alpha,\beta$-unsaturated ester to the cobalt;

Yd (%) denotes the number of mols of the product in question per 100 mols of diesters and of saturation ester formed;

DC (%) denotes the number of mols of diesters and of saturated ester formed per 100 mols of starting material introduced;

T (°C) denotes the temperature in degrees centigrade;

A denotes the activity expressed in mols of diesters and of saturated ester formed per hour and per gram atom of cobalt;

X (%) denotes the number of mols of diesters per 100 mols of products formed;

Y (%) denotes the number of mols of alkyl adipate per 100 mols of products formed; and Z (%) denotes the number of mols of alkyl pentanoate per 100 mols of products formed.

The products formed do not include the compounds resulting from the isomerization of the olefinic double bond. The products formed are essentially the diesters and the alkyl pentanoate, the latter resulting from the hydrogenation of the starting material ester.

EXAMPLE 1

50 millimols of methyl crotonate, 102 millimols of methanol, 1 millimol of dicobalt octacarbonyl and 7.9 millimols of isoquinoline were introduced into a 125 ml stainless steel autoclave purged under a stream of argon. The autoclave was then purged with a stream of carbon monoxide containing 0.7% by volume of hydrogen, and it was then heated to 160° C. under a pressure of 130 bars.

After a reaction time of 2 hours at this temperature, the autoclave was cooled and degassed. The reaction mixture was analyzed by gas chromatography.

The results obtained were as follows:

DC (%)=77.9; (A=9.7)

|  |  | Yd (%) |
|---|---|---|
| (i) | Dimethyl glutarate | 77.0 |
| (ii) | Dimethyl 2-methylsuccinate and dimethyl 2-ethylmalonate | 18.0 |
| (iii) | Methyl butanoate | 5.0 |

EXAMPLE 2

Example 1 was repeated, but with the methyl crotonate being replaced by an equivalent amount of methyl oct-2-enoate.

The following results were obtained:

DC (%)=37.6; (A=4.7)

|  |  | Yd (%) |
|---|---|---|
| (i) | Dimethyl nonanedioate | 53.2 |
| (ii) | Branched saturated diesters | 30.0 |
| (iii) | Methyl octanoate | 16.8 |

EXAMPLE 3

Using the autoclave and the procedure described above, an experiment was carried out on a charge consisting of 80 millimols of methyl hex-2-enoate, 200 millimols of methanol, 0.68 millimol of dicobalt octacarbonyl and 5.5 millimols of isoquinoline. The results obtained after a reaction time of two hours at 160° C., under 130 bars and using carbon monoxide containing 1.2% by volume of hydrogen, were as follows:

DC (%)=50.2; (A=14.8)

|  |  | Yd (%) |
|---|---|---|
| (i) | Dimethyl heptanedioate | 74.3 |
| (ii) | Branched saturated diesters | 19.7 |
| (iii) | Methyl hexanoate | 5.6 |

EXAMPLES 4 to 8

A first series of experiments was carried out, using the procedure described above, by reacting carbon monoxide containing 0.8% (by volume) of hydrogen with a charge containing 80 millimols of methyl pent-2-enoate, 200 millimols of methanol, 0.6 millimol of dicobalt octacarbonyl and some isoquinoline. The particular conditions, and also the results obtained after a reaction time of 2 hours at 160° C., under 130 bars, are reported in Table I below.

TABLE I

| Example No. | N/Co | A | X (%) | Y (%) | Z (%) |
|---|---|---|---|---|---|
| 4 | 3.6 | 18 | 93.4 | 76.4 | 5.9 |
| 5 | 8.2 | 22 | 94.7 | 78.4 | 5.9 |
| 6 | 13.2 | 13 | 95.5 | 77.6 | 4.3 |
| 7 | 19.2 | 13 | 93.4 | 75.7 | 6.5 |
| 8 | 20.1 | 13 | 94.7 | 76.8 | 7.4 |

CONTROL EXPERIMENTS (a) to (d)

A second series of experiments was carried out, using the procedure described above, by reacting carbon monoxide containing 0.8% (by volume) of hydrogen with a charge containing 80 millimols of methyl pent-3-enoate, 200 millimols of methanol, 0.6 millimol of dicobalt octacarbonyl and some isoquinoline. The particular conditions, and also the results obtained after a reaction time of 2 hours at 160° C., under 130 bars, are reported in Table II below.

TABLE II

| Reference | N/Co | A | X (%) | Y (%) | Z (%) |
|---|---|---|---|---|---|
| a | 3.7 | 7.8 | 94.9 | 76.0 | 6.6 |
| b | 7.4 | 7.4 | 95.1 | 80.0 | 4.3 |
| c | 13.4 | 3.9 | 95.4 | 79.5 | 3.7 |
| d | 20.5 | 3.7 | 92.4 | 78.4 | 7.4 |

EXAMPLES 9 to 14

CONTROL EXPERIMENTS (e) to (j)

The conditions and the results of a series of experiments carried out using the procedure described above are reported in Table III below. Isoquinoline, methanol, dicobalt octacarbonyl and carbon monoxide containing 0.8% (by volume) of hydrogen were used in all of the experiments. The reaction time was 2 hours. In Examples 8 to 13, methyl pent-2-enoate was used as the starting material; control experiments (e) to (j) were carried out using methyl pent-3-enoate.

In Table III, P denotes the pressure at the temperature of the experiment.

TABLE III

| Example No. | CH$_3$OH millimols | Co$_2$(CO)$_8$ millimols | =/Co | N/Co | T °C. | P bars | DC (%) | X (%) | Y (%) |
|---|---|---|---|---|---|---|---|---|---|
| 9 | 98 | 0.99 | 25.2 | 4.0 | 160 | 90 | 60.9 | 90.1 | 75.9 |
| e | 104 | 1.01 | 25.1 | 4.2 | 160 | 90 | 33.5 | 89.3 | 75 |
| 10 | 100 | 0.93 | 26.7 | 4.3 | 140 | 130 | 66.0 | 94.5 | 69.6 |
| f | 100 | 1.03 | 24.0 | 3.8 | 140 | 130 | 28.1 | 94.0 | 70.3 |
| 11 | 148 | 0.41 | 122 | 3.7 | 160 | 130 | 23.7 | 95.7 | 78.6 |
| g | 148 | 0.42 | 120 | 3.9 | 160 | 130 | 12.9 | 94.2 | 77.7 |
| 12 | 102 | 1.03 | 24 | 19.4 | 160 | 130 | 34.9 | 85.2 | 67.2 |
| g | 104 | 0.98 | 25 | 20.6 | 160 | 130 | 9.0 | 90.1 | 79.7 |
| 13 | 202 | 0.2 | 240 | 19.6 | 180 | 280 | 11.0 | 90.8 | 77.6 |
| i | 199 | 0.2 | 240 | 20.3 | 180 | 280 | 1.4 | 90.5 | 71.5 |
| 14 | 200 | 0.5 | 100 | 4 | 180 | 250 | 54.5 | 93.7 | 74.5 |
| j | 198 | 0.495 | 101 | 4.1 | 180 | 250 | 32.6 | 93.3 | 75.7 |

EXAMPLE 15

A mixture consisting of 482 millimols of methyl pent-2-enoate, 1,050 millimols of methanol, 3.45 millimols of dicobalt octacarbonyl and 27.6 millimols of isoquinoline was introduced into a 300 ml stainless steel reactor equipped with a central stirring turbine and heated and regulated electrically. The reactor was heated to 160° C. while being swept with carbon monoxide containing 0.8% by volume of hydrogen. The pressure in the autoclave was maintained at 130 bars and the rate of feed of the gaseous mixture was 40 liters/hour (NTP conditions). Samples of the reaction mixture were taken periodically and analyzed.

The results obtained are reported in Table IV below, in which the time in hours indicates the interval of time elapsing between the attainment of the reaction temperature (160° C.) and the removal of the sample in question.

The Table also indicates, in the column headed "Control k", the value of the various corresponding DC (%) obtained in another experiment carried out as in Example 15, but utilizing a mixture consisting of 700 millimols of methyl pent-3-enoate, 1,525 millimols of methanol, 40 millimols of isoquinoline and 5 millimols of dicobalt octacarbonyl.

TABLE IV

| SAMPLE No. | TIME (hours) | X (%) | EXAMPLE 15 Y (%) | EXAMPLE 15 DC (%) | Control k DC (%) |
|---|---|---|---|---|---|
| 1 | 0.5 | 95.9 | 79.3 | 18.6 | 6.3 |
| 2 | 1 | 95.2 | 78.0 | 34.5 | 13.1 |
| 3 | 2 | 93.7 | 75.3 | 58.4 | 28 |
| 4 | 3 | 93.7 | 75.2 | 75.2 | 45 |
| 5 | 4 | 93.3 | 74.2 | 88.3 | 60.7 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims. What is claimed is:

1. A process for the preparation of a linear saturated diester having the structural formula (I):

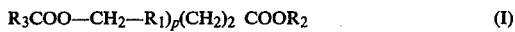

$$R_3COO\text{---}CH_2\text{---}R_1)_p(CH_2)_2\ COOR_2 \qquad (I)$$

comprising reacting, in liquid phase, carbon monoxide and an alcohol of the formula $R_3OH$ with an $\alpha,\beta$-unsaturated ester having the structural formula (II):

$$CH_3\text{---}R_1)_p\ CH\text{=}CH\text{---}COOR_2 \qquad (II)$$

wherein said formulae (I) and (II), $R_1$ is an alkylene radical having up to 20 carbon atoms, or such radical substituted by one or two chlorine atoms or alkoxy substituents having up to 4 carbon atoms; $R_2$ is an alkyl radical having up to 12 carbon atoms, or such radical substituted by one or two hydroxyl substituents, an aralkyl substituent having from 7 to 12 carbon atoms, or a phenyl substituent; p is zero or one; and $R_3$ is defined as was $R_2$, and further wherein $R_2$ and $R_3$ may be identical or different; in the presence of (i) a catalytically effective amount of a metallic cobalt or cobalt compound catalyst, and (ii) a tertiary nitrogencontaining base.

2. The process as defined by claim 1, the temperature of reaction ranging from 100° to 200° C.

3. The process as defined by claim 2, the reaction being carried out under a pressure ranging from 50 to 1,000 bars.

4. The process as defined by claim 1, wherein the $\alpha,\beta$-unsaturated ester having the structural formula (II), $R_1$ is a radical—$(CH_2)_n$, with n being an integer ranging from 1 to 6, or such radical substituted by one or two methyl substituents.

5. The process as defined by claim 4, wherein the $\alpha,\beta$-unsaturated ester having the structural formula (II), $R_2$ is an alkyl radical having up to 4 carbon atoms.

6. The process as defined by claim 1, wherein the $\alpha,\beta$-unsaturated ester having the structural formula (II) is an alkyl pent-2-enoate in which the alkyl moiety contains up to 4 carbon atoms.

7. The process as defined by claim 1, wherein the tertiary nitrogen-containing base (ii) is a 5-membered or 6-membered nitrogen-containing heterocyclic compound, or such heterocycle substituted by one or two alkyl or alkoxy substituents having up to 4 carbon atoms, or one or two hydroxyl substituents or halogen atoms, optionally comprising two or three double bonds, and which heterocycle can be fused to a benzene nucleus, with the proviso that the adjacent atoms bonded to the nitrogen hetero-atom are neither substituted nor common to two ring nuclei.

8. The process as defined by claim 7, said nitrogen heterocycle (ii) having a $pK_a$ ranging from 3 to 10.

9. The process as defined by claim 8, said nitrogen heterocycle (ii) being a 6-membered heterocycle having a $pK_a$ ranging from 4 to 7.

10. The process as defined by claim 1, wherein the molar ratio of the $\alpha,\beta$-unsaturated ester (II) to the cobalt catalyst (i) ranges from 10 to 1,000.

11. The process as defined by claim 10, wherein the molar ratio of the alcohol to the $\alpha,\beta$-unsaturated ester (II) ranges from 1 to 10.

12. The process as defined by claim 11, wherein the molar ratio of the tertiary nitrogen-containing base (ii) to the cobalt catalyst (i) ranges from 0.5 to 50.

13. The process as defined by claim 1, wherein the alcohol $R_3OH$ is methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol or phenol.

14. The process as defined by claim 1, wherein the catalyst (i) is metallic cobalt, an organic or inorganic salt of cobalt, or a cobalt carbonyl or hydrocarbonyl.

15. The process as defined by claim 1, wherein the tertiary nitrogen-containing base (ii) is pyridine, 4-picoline, isoquinoline, 3,5-lutidine or 3,4-lutidine.

16. The process as defined by claim 2, said reaction temperature ranging from 130° to 180° C.

17. The process as defined by claim 3, said reaction pressure ranging from 100 to 300 bars.

18. The process as defined by claim 10, said molar ratio ranging from 20 to 300.

19. The process as defined by claim 11, said molar ratio ranging from 2 to 5.

20. The process as defined by claim 12, said molar ratio ranging from 2 to 25.

* * * * *